(12) United States Patent
Suslov

(10) Patent No.: US 7,361,175 B2
(45) Date of Patent: Apr. 22, 2008

(54) PLASMA SURGICAL DEVICE

(75) Inventor: Nikolay Suslov, Västra Frölunda (SE)

(73) Assignee: Plasma Surgical Investments Limited, Tortola (VG)

( * ) Notice: Subject to any disclaimer, the term of this patent is extended or adjusted under 35 U.S.C. 154(b) by 431 days.

(21) Appl. No.: 10/528,061

(22) PCT Filed: Oct. 2, 2003

(86) PCT No.: PCT/SE03/01537

§ 371 (c)(1),
(2), (4) Date: Mar. 15, 2005

(87) PCT Pub. No.: WO2004/030551

PCT Pub. Date: Apr. 15, 2004

(65) Prior Publication Data

US 2006/0004354 A1    Jan. 5, 2006

(30) Foreign Application Priority Data

Oct. 4, 2002    (SE) ................................. 0202958

(51) Int. Cl.
*A61B 18/14*    (2006.01)
(52) U.S. Cl. ..................................................... 606/49
(58) Field of Classification Search .............. 606/49
See application file for complete search history.

(56) References Cited

U.S. PATENT DOCUMENTS

| 3,434,476 A | 3/1969 | Shaw et al. |
| 3,858,072 A | 12/1974 | Dembovsky |
| 3,938,525 A | 2/1976 | Coucher |
| 5,320,621 A | 6/1994 | Gordon et al. |
| 5,843,079 A * | 12/1998 | Suslov .................. 606/43 |
| 6,475,215 B1 | 11/2002 | Tanrisever |

FOREIGN PATENT DOCUMENTS

WO    WO 96/06572 A1    3/1996

OTHER PUBLICATIONS

International Search Report and International Preliminary Examination Report.

* cited by examiner

*Primary Examiner*—Lee S. Cohen
(74) *Attorney, Agent, or Firm*—Harness, Dickey & Pierce, P.L.C.

(57) ABSTRACT

A plasma surgical device for reducing bleeding in live tissue by means of a gas plasma. The device comprises a plasma-generating system having an anode (1), a cathode (8) and a gas supply channel (17) for supplying gas to the plasma-generating system, the plasma-generating system comprising at least one electrode (3, 5), which is arranged between said cathode (8) said anode (1), and the plasma-generating system being enclosed by a housing (12) of an electrically conductive material, which is connected to the anode (1). The device is characterised in that said housing (12) forms said gas supply channel (17).

28 Claims, 6 Drawing Sheets

PLASMA SURGICAL DEVICE

FIELD OF THE INVENTION

The present invention relates to a plasma surgical device for reducing bleeding in live tissue by means of a gas plasma, comprising a plasma-generating system having an anode, a cathode and a gas supply channel for supplying gas to the plasma-generating system, the plasma-generating system further comprising at least one electrode, which is arranged between said cathode and said anode, and the plasma-generating system being enclosed by a housing of an electrically conductive material, which is connected to the anode.

BACKGROUND ART

Plasma surgical devices here means devices of the kind used in surgery to stop bleeding by means of a gas plasma. Such gas-plasma-producing devices have the shape of a pen that can be easily applied to a desired area, for example bleeding tissue. At the tip of the pen, a gas plasma is present, the very high temperature of which causes coagulation and a haemostatic effect by a necrosed layer being formed like a crust over the tissue adjacent to the tip.

WO 96/06572 (Suslov) discloses a plasma surgical device according to prior art. This device has an electrically conductive body, which is connected to a positive pole of an energy source having a positive potential. Moreover, the body is formed with a cylindrical channel designed to heat the plasma-generating gas, which channel is formed from a number of sections that are electrically insulated from each other. The device has a cathode consisting of an electrically conductive tube, on one end of which an electrode is mounted. The other end of the tube is connected to a negative pole of an energy source. This end of the tube is also connected to a gas supply unit to allow gas to be supplied to the device through the cathode tube.

In use, gas is supplied to the device through the cathode tube, while at the same time a voltage is applied across the positive and the negative pole, so that a voltage difference is obtained between the cathode and the electrically conductive body. Initially, the voltage difference generates an electric arc, which heats the gas supplied to form a plasma, which is then maintained.

U.S. Pat. No. 3,991,764 (Incropera, et al) discloses another device according to prior art. Here as well gas is supplied through a tube that is electrically connected to the cathode of the device and runs into said cathode. Here the anode of the device is realised by a conductive body, which in turn is enclosed by a housing. Furthermore, water lines are provided for cooling the device.

A further device of this type is disclosed in WO 92/19166 (Nauchno-Issledovatelsky Institut).

Owing to the recent developments in surgical technology open surgery is being used less and less, whereas laparoscopic (key-hole) surgery is being used more often. This implies new demands on the instruments used, in particular it must be possible to manufacture relatively small instruments. Similarly, increased efficiency requirements in medical care have lead to the abandonment of instruments that require special processes, for example sterilisation, after each use.

The object of the present invention is therefore to provide a plasma surgical device which satisfies one or more of the requirements stated above.

SUMMARY OF THE INVENTION

The above object is achieved by means of a device as described by way of introduction, in which the housing forms said gas supply channel.

This construction allows less bulky instruments to be designed, which facilitates their use in laparoscopic surgery. Furthermore, it allows cost-efficient manufacturing of the instruments, thereby making it possible to make them available as ready-sterilized, disposable instruments.

Suitably, the housing forms, in addition to said gas supply channel, an additional channel. This channel can be used for different purposes, conveniently to allow a fluid to flow through it. For example, the additional channel can be used for supplying or discharging a coolant or for removing liquids from an area where surgery is performed, etc.

Preferably, the housing forms, in addition to said gas supply channel, at least two additional channels. This design is particularly simple and space-saving. Advantageously, the gas supply channel can be centrally mounted in the housing, and the additional channels arranged along the circumference of the gas supply channel. In this case, the additional channels are preferably cooling channels for respectively supplying and discharging a coolant.

Thus, one way of describing it is that the housing forms a supply portion, in which said gas supply channel is formed, and a plasma-generating portion, in which said plasma-generating system is provided. This means that the cross section of the housing in the gas supply portion can be such as to form one or more channels, whereas the cross section in the plasma-generating portion is such as to allow for the plasma-generating system. The length of the different portions can be varied depending on the application for which the device is intended.

The plasma-generating system comprises, in per se known manner, a cathode which is connected to a conductor for connection to a source of electric energy. Preferably, said conductor extends through any one of the channels in said tubular housing, suitably through a centrally arranged gas supply channel. The gas will then flow about the conductor towards the plasma-generating system and the cathode.

The plasma-generating system further comprises at least one electrode, which is mounted between said cathode and anode. Preferably, the plasma-generating system comprises at least two electrodes, which are insulated from each other by an insulating means. By using two electrodes that are insulated from each other the risk of undesirable, double electric arcs being generated in the system is reduced. The electrode or electrodes, and any insulators, are suitably of annular cross section and form a channel in which the plasma is heated between the cathode and the anode.

The electrodes, and any insulators, are conveniently mounted in a holding means of an electrically insulating material. To ensure easy manufacture and a reliable construction, the electrodes, and any insulators, can advantageously be press fitted to said holding means.

Moreover, the cathode holder can suitably be mounted in such manner in the holding means that the cathode is positioned concentrically with and spaced from an electrode closest to the cathode, advantageously by the cathode being mounted in the holding means with the aid of a cathode holder that is press fitted to the holding means.

In this way, the holding means forms a convenient assembly unit for keeping the electrodes and insulators together and for ensuring that the cathode is kept in the correct position relative thereto. To prevent the holding means from being damaged because of the very high temperatures occur-ring around the cathode (up to 3200° C.), an insulating tube of a ceramic material is conveniently mounted on the inside of the holding means so as to enclose the cathode, for the protection of the holding means.

Furthermore, the holding means suitably has a connection end, which is connected to said gas supply channel, so that gas is passed through the holding means to the cathode and then on through said at least one electrode towards the anode. However, the holding means preferably has an outer shape that allows a fluid to flow respectively from and to the additional channels, so that the fluid can reach a space formed between the holding means, including said electrode and any insulators, and the inner wall of the tubular housing. Thus, the outer shape of the holding means should not block the outlets and inlets, respectively, of the additional channels in the plasma-generating portion.

Suitably, a gasket can be provided between the anode and an electrode closest to the anode. In this case, the plasma-generating system is arranged in such manner in the housing that the anode is connected to the housing, a predetermined compressive force being applied to the gasket. In this way, a watertight seal is ensured between the housing and the anode and electrical contact is established between the two.

Moreover, the housing can be surrounded by a first contact ring that is in electrical contact therewith, which contact ring is connected to earth. This makes the instruments safer for the user. In this case, a second contact ring, which is electrically connected to the housing, may also be provided, which ring is capable of being used to constantly control the earthing of the housing.

Suitably, a connecting device is provided for connecting the gas supply to said gas supply channel and any desired function to the additional channels, such as the supply of coolant or suction power for evacuating liquid. The connecting device can have an outlet end, which defines connecting channels for obtaining a fluidtight fit in said gas supply channel and additional channels, and an inlet end provided with hose couplings for connecting hoses to each of said connecting channels. Furthermore, the connecting device can also have a conductor opening through which the cathode conductor can extend for connection to a voltage source. In this way, the device can be easily connected to one or more supply units, adapted to supply, for example, energy, gas and coolant supply, etc.

Moreover, the device can suitably comprise a handle portion, which at least partially encloses said housing for easy handling of the device.

To allow different kinds of devices to be connected to one and the same supply unit, adapted to supply, for example, gas, coolant or energy, the device can advantageously comprise a circuit adapted to distinguish the type of device. This circuit comprises a component whose electric resistance is selected to represent the device type. Advantageously, the electric resistance can be read with reference to one of the earthed contact rings. By reading the electric resistance an indication of what kind of device is connected to the supply unit is obtained. Examples of different kinds of devices are instruments intended for open surgery and instruments intended for laparoscopic surgery.

Further features and advantages of the present invention will be apparent from the following description of one particular embodiment of the invention, reference being made to the accompanying drawings.

DESCRIPTION OF A PREFERRED EMBODIMENT OF THE INVENTION

Figure 1:
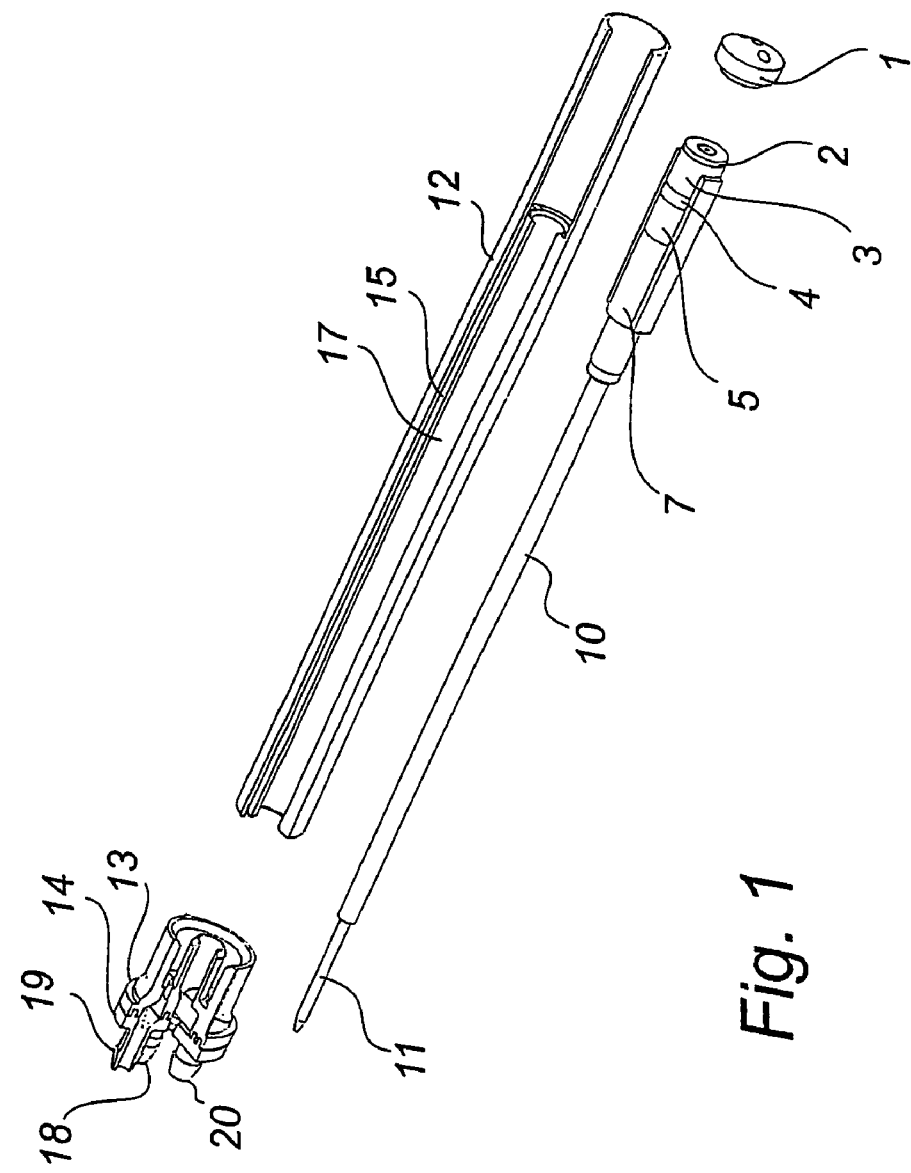
FIG. 1 is an exploded view of one embodiment of the device according to the invention.

FIG. 1 is an exploded view of one embodiment of a plasma surgical device according to the invention. The device comprises an elongate housing 12, which encloses a plasma-generating system for generating a plasma that is discharged at the end of the housing 12 and used to stop bleeding.

FIG. 1 illustrates the housing 12 as removed from the plasma-generating system. As shown in FIG. 1 the housing has a supply portion (furthest away in the figure) and a plasma-generating portion (in the foreground of the figure), in which the plasma-generating system is mounted. The supply portion forms a gas supply channel 17 and, in this case, two additional channels 15, 16, which are used as cooling channels. The housing 12 is here formed from a tubular section.

Figure 2:
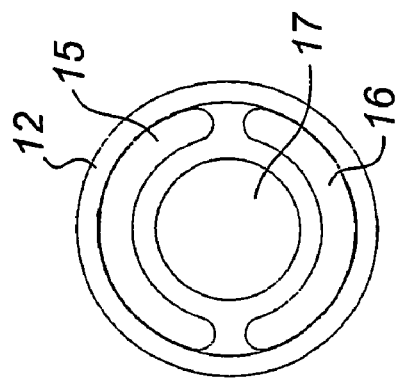
FIG. 2 is a view seen from the plasma-generating portion of the housing of the device shown in FIG. 1.

FIG. 2 illustrates the housing 12 as seen from the end of the plasma-generating portion (in the foreground of the figure). This view shows the cross section of the supply portion of the housing 12. The gas supply channel 17 is arranged at the centre of the tubular housing 12 and the cooling channels 15, 16 are arranged along the circumference of the gas supply channel 17. Here the gas supply channel 17 is circular in cross section, whereas the cooling channels 15, 16 are C-shaped in cross section and together extend along the greater part of the circumference of the gas supply channel 17.

In the plasma-generating portion, the housing 12 is single circular in cross section and formed by an extension of the outer walls of the cooling channels 15, 16.

The housing 12 is formed of an electrically conductive material, suitably one that is appropriate for manufacturing units with the above-described cross sections, such as aluminium.

FIG. 1 also shows the plasma-generating system lying beside the housing 12. The system comprises an anode 1, a cathode 8 (see FIG. 3) and a set of electrodes 3, 5 disposed therebetween. The electrodes 3, 5 are annular and form, in per se known manner, a channel in which the plasma is heated before it is discharged at the anode 1.

Figure 3:
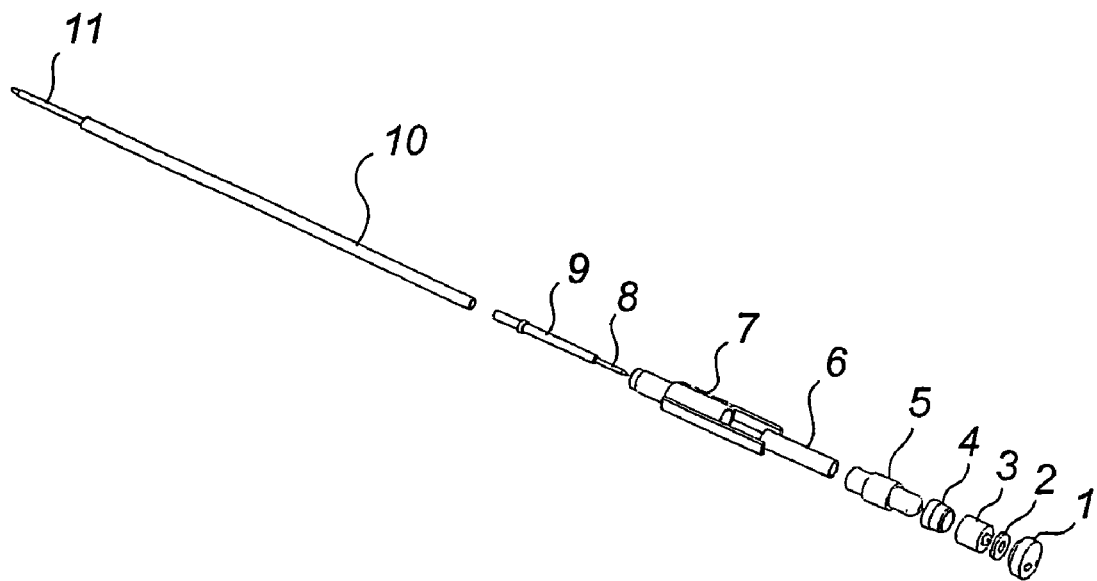
FIG. 3 is an exploded view of the cathode conductor and the plasma-generating system of the device shown in FIG. 1.

FIG. 3 shows more clearly the plasma-generating system. The system comprises a cathode 8, which is mounted in a cathode holder 9, which in turn is connected to an electrical conductor 11 for connection to a source of electric energy. The conductor 11 is enclosed by an insulator 10.

The cathode holder 9 is designed to be fitted in a certain position in a holder element 7, which is formed of an insulating material, such as a temperature resistant plastic material. To protect the holder element 7 from the high temperatures (up to 3200° C.) that may occur around the cathode, a cylindrical insulating tube 6 is provided in the holder element 7, between the cathode 8 and the inside of the holder element 7. Suitably, the insulating tube 6 is made of a heat-insulating ceramic material.

Figure 4:
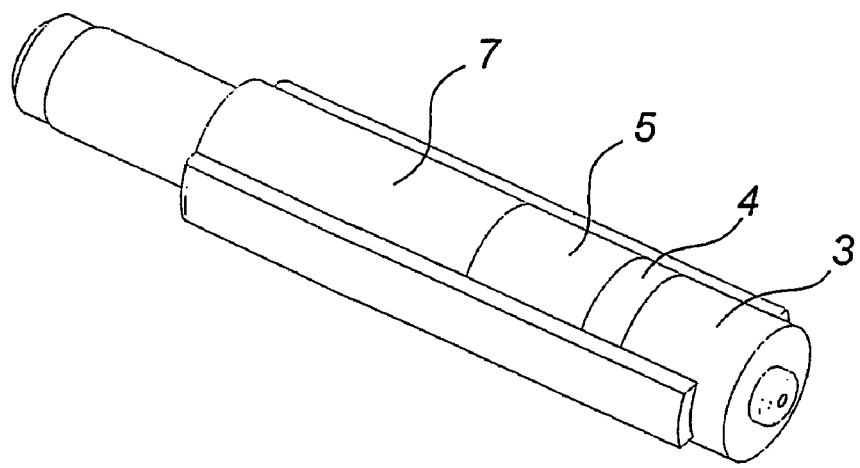
FIG. 4 illustrates the holding element, with electrodes, of the device shown in FIG. 1.
Figure 5:
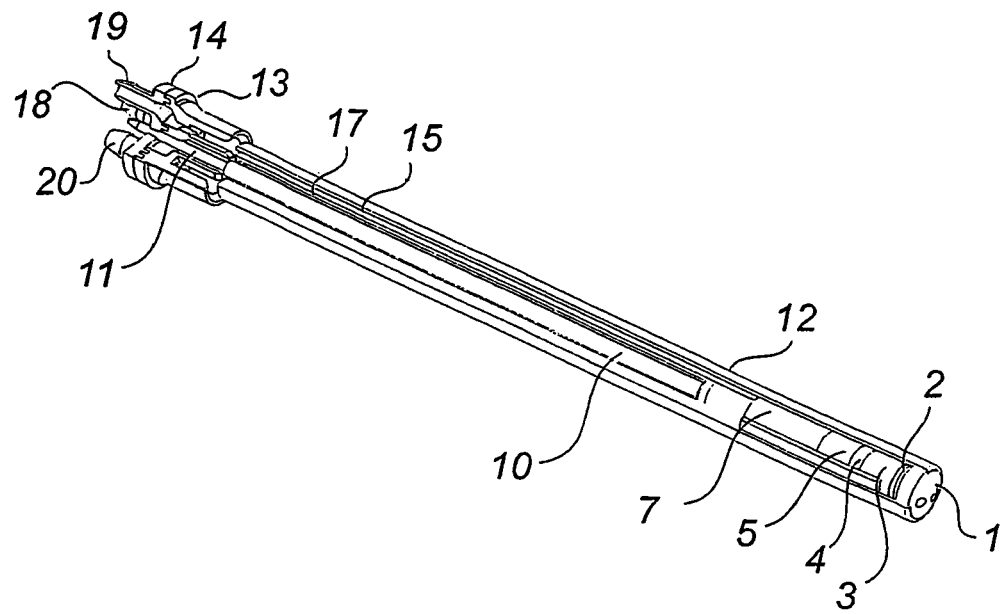
FIG. 5 illustrates the device in FIG. 1 when assembled, the plasma-generating system being exposed.
Figure 6:
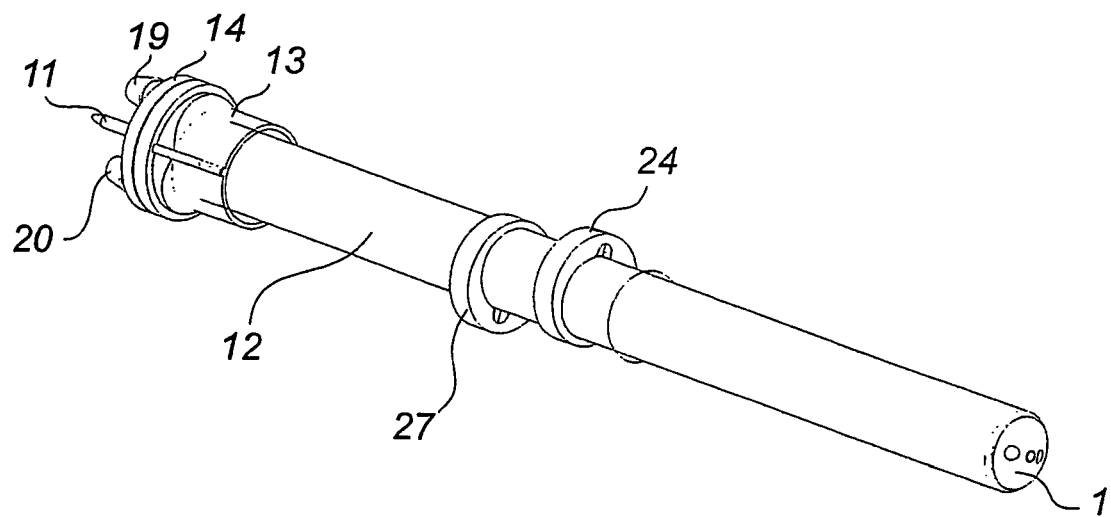
FIG. 6 illustrates the device in FIG. 1 when assembled.

Furthermore, electrodes 5, 3, separated by insulators 4, are arranged in the holding means in such manner that they form a channel for heating the plasma. Here, two electrodes 5, 3 are provided, which are separated by one insulator. The shape of the electrodes as well as the channel diameter can be adapted to any desired purpose. The first electrode 5, the insulator 4 and the second electrode 3 are press fitted together. Furthermore, the electrodes 5, 3 and the insulator 4 are here press fitted to the holder element 7. In FIG. 4, the electrodes 5, 3 and the insulator 4 are shown when mounted in the holder element 7.

The holder element 7 is here conveniently designed according to the purpose, with a cylindrical part for connection to the cathode holder 9, and outwardly extending arms between which the electrodes 5, 3 and the insulator 4 can be press fitted. The connection to the cathode holder 9 is such that the cathode 8 is arranged concentrically with and spaced from the electrode 5 closest to the cathode 8.

The electrode 3 furthest away from the cathode 8 is in contact with an annular gasket 2, which in turn bears against the anode 1.

When assembled, the holder element 7, with the cathode holder 9, is mounted in the plasma-generating portion of the tubular housing 12. The conductor 11 connected at the cathode, and the insulation 10 associated therewith, extends through the gas supply channel 17 in the supply portion of the housing. The anode 1 is connected to the housing 12 and the plasma-generating system has such dimensions relative to the housing 12 that a predetermined compressive force is exerted on the gasket 2 between the anode 1 and the electrode 3 closest thereto. This ensures that a watertight seal is obtained between the anode and the housing 12. The controlling compressive force can be achieved by means of threading between the anode 1 and the housing 12, welding or soldering. In any case, the interconnection of the anode 1 and the housing 12 is such as to provide an electrical contact between the two.

To provide a connection to the gas supply channel 17 the cylindrical portion of the holder element 7 that encloses the cathode 8 is designed to fit in the gas supply channel 17. Moreover, the size of the electrodes and the shape of the arms of the holder element are such as not to prevent the coolant from flowing out and in through the cooling channels 15, 16 and on between the electrodes 5, 3 and the inner wall of the housing 12. The coolant is preferably water, although other fluids are conceivable.

Moreover, to provide a connection to supply units for supplying plasma-generating gas, energy and coolant, a coupling device is provided (detached in FIG. 1). The coupling device comprises two parts, an outlet end 13, which defines coupling channels to be fitted in the channels 15, 16, 17 of the tubular housing 12, and an inlet end 14 provided with hose couplings 18, 19, 20 for coupling hoses to each of said coupling channels. The hose couplings 18, 19, 20 can, for example, be "olive couplings". Furthermore, the coupling device is provided with a conductor opening through which the conductor 11 extends for connection to an energy source.

Figure 7:
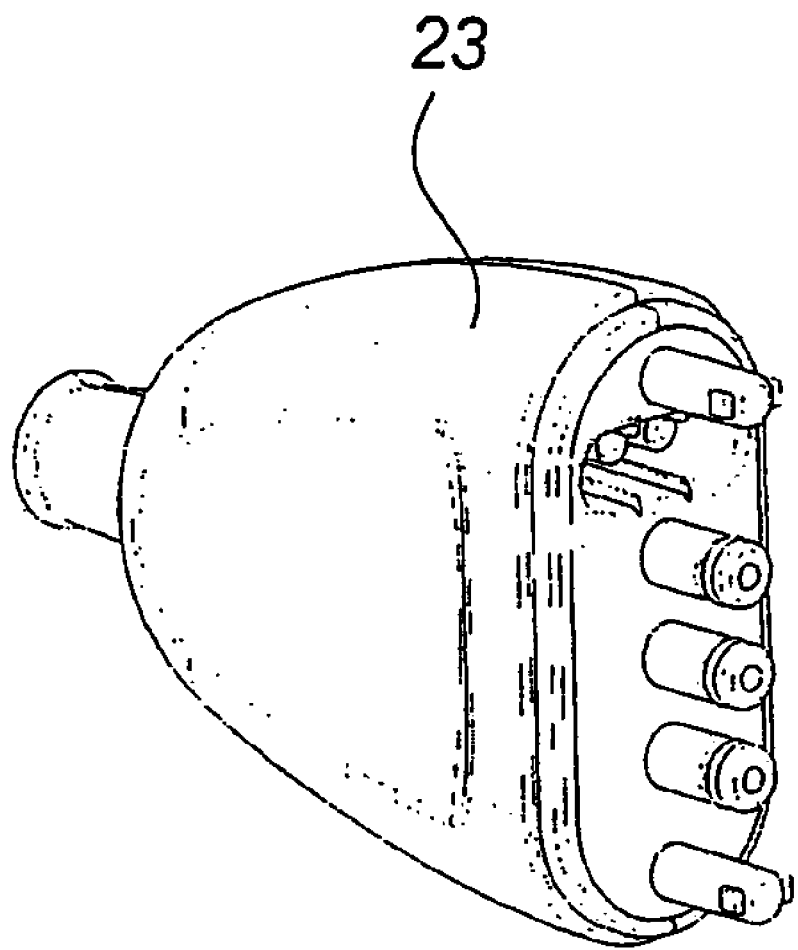
FIG. 7 illustrates a coupling terminal adapted to effect a connection to a supply unit adapted to supply gas, coolant and energy.

From the hose couplings 18, 19, 20, flexible hoses conveniently extend to a coupling terminal for connection to a supply unit. FIG. 7 illustrates one example of such a coupling terminal.

Figure 8:
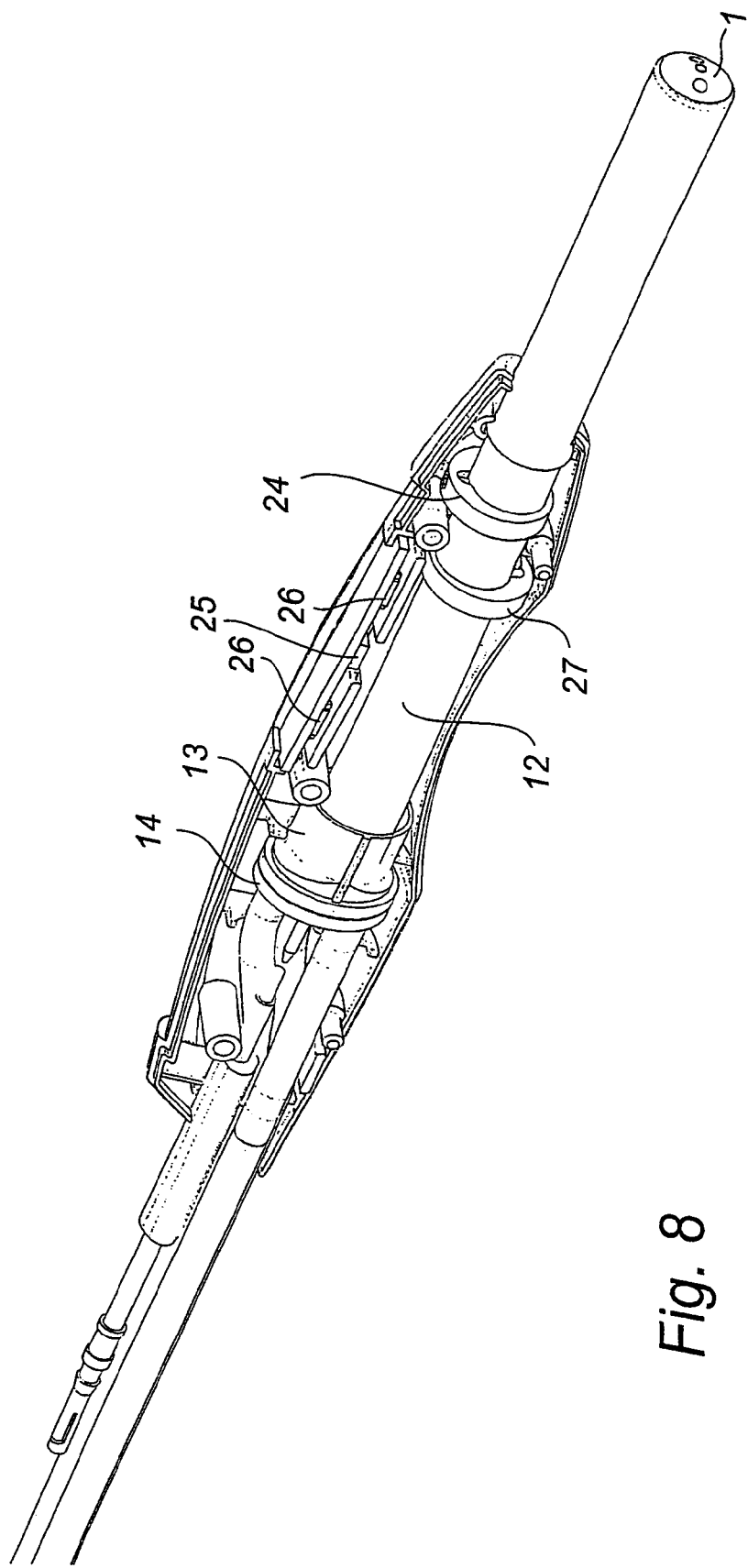
FIG. 8 illustrates the mounting of the device in FIG. 1 in a handle portion.

FIG. 8 shows the device in FIG. 1 when assembled with a handle portion. In the drawing, one half of the handle portion has been removed, so that the connection to other parts can be seen clearly. The handle portion partially encloses the housing 12 and extends over the coupling device and over a portion of the supply hoses. The housing 12 is here provided with a first contact ring 27, which is connected to earth. This is to ensure that the device has zero potential. In addition, the housing is provided with a second contact ring 24, which is usable to control the earthing of the housing 12.

The handle portion further comprises a printed circuit card 25, which contains, inter alia, an indication component, whose electrical resistance can be read and used to indicate what type of device is being used. In this embodiment, the handle portion is also provided with buttons 26 to switch the device on and off.

Figure 9:
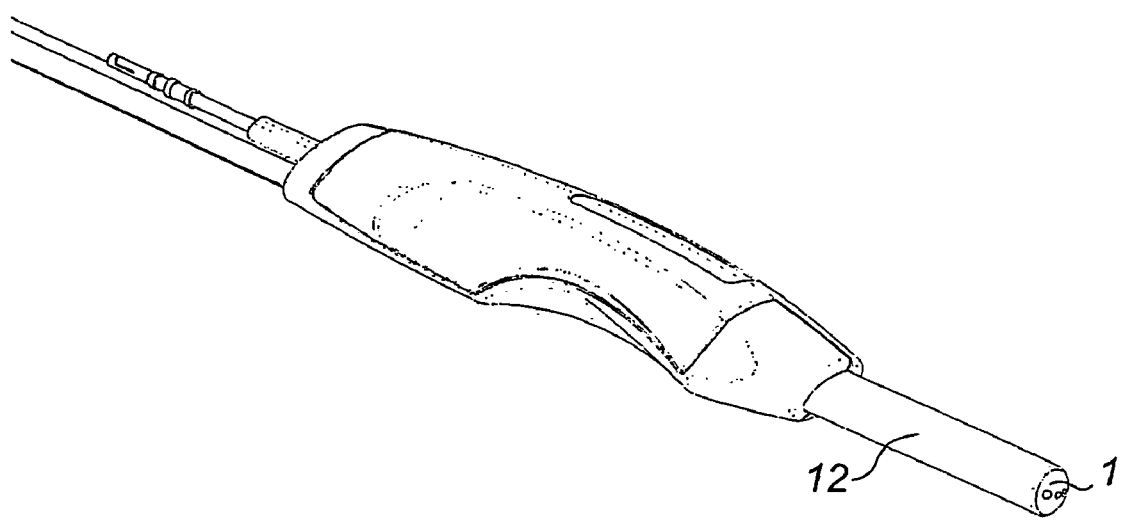
FIG. 9 illustrates the device with the handle portion according to FIG. 8.

FIG. 9 shows the device in FIG. 8 with the whole handle portion. The handle has an ergonomic design that allows it to be held and operated comfortably.

Figure 10:
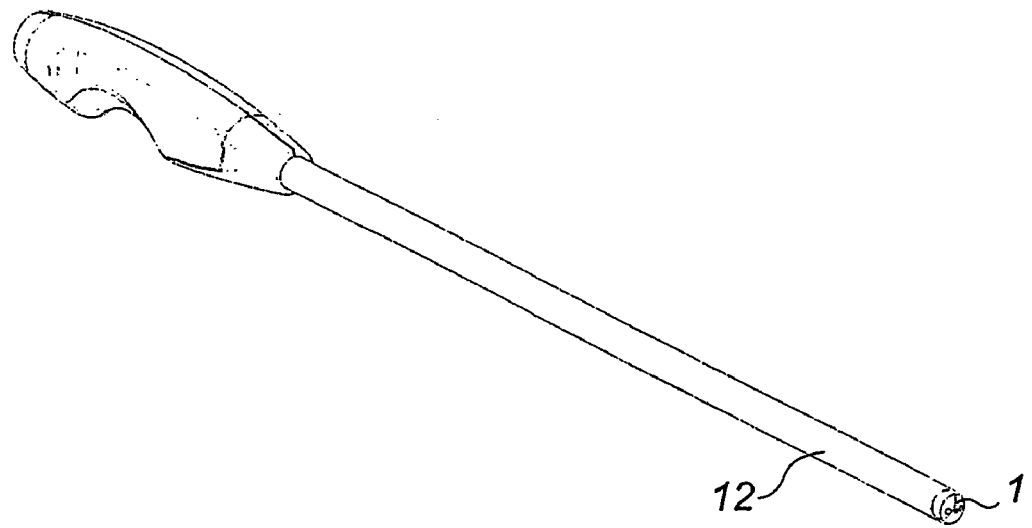
FIG. 10 illustrates a second embodiment of a device according to the invention.

FIG. 10 illustrates a second embodiment of the invention. The tubular housing 12 is here longer than in the embodiment described previously, and the shape of the handle is slightly different. This embodiment is particularly suitable for laparoscopic surgery. The handle portion does not have any buttons and instead the device is switched on and off by means of a footswitch.

Advantageously, the device can be provided as a disposable instrument. The whole device, including housing, coupling device, hoses and coupling terminal, can be sold as a disposable instrument. Alternatively, only the housing and its content may be disposable, and adapted to be connected to non-disposable handles and hoses, etc.

Advantageously, the plasma-generating gas is the same type of gases that are used in prior-art instruments, for example argon.

Other embodiments and variants are conceivable within the scope of the present invention. For example, the number and design of the electrodes may be varied depending on the type of plasma-generating gas used and the desired properties of the plasma. Moreover, the length of the housing, and of its supply portion and plasma-generating portion, respectively, may be varied to fit different applications. The coupling device may be designed in several ways just like the handle. The number of additional channels and their cross section may be varied. For example, three additional channels may be provided, two being used for supplying and discharging a coolant and one being used for sucking liquid from an area of surgery. Furthermore, the housing and the anode may be made in one piece rather than as two units put together according to the embodiment described above.

The invention claimed is:

1. A plasma surgical device for reducing bleeding in living tissue by means of a gas plasma, comprising:
    a plasma-generating system having an anode, a cathode and a gas supply channel for supplying gas to the plasma-generating system, the plasma-generating system having at least one electrode, which is arranged between said cathode and said anode, and the plasma-generating system being enclosed by a housing of an electrically conductive material, which is connected to the anode, wherein said housing forms said gas supply channel.

2. A plasma surgical device according to claim 1, in which said housing, in addition to said gas supply channel, forms at least one additional channel.

3. A plasma surgical device according to claim 2, in which said housing, in addition to said gas supply channel, forms at least two additional channels.

4. A plasma surgical device according to claim 3, in which said gas supply channel is arranged at the centre of the housing and the additional channels are arranged along the circumference of the gas supply channel.

5. A plasma surgical device according to claim 3, in which said additional channels are cooling channels for supplying and discharging a coolant.

6. A plasma surgical device according to claim 2, in which a connecting device is provided for connecting the gas supply to said gas supply channel and any desired function to said additional channels.

7. A plasma surgical device according to claim 6, in which said connecting device has an outlet end, which defines connecting channels for obtaining a fluidtight fit in said gas supply channel and additional channels, and an inlet end provided with hose couplings for connecting hoses to each of said connecting channels.

8. A plasma surgical device according to claim 6, in which said connecting device also has a conductor opening through which a cathode conductor extends for connection to a voltage source.

9. A plasma surgical device according to claim 2, in which said housing is connected to hoses for supplying gas and any desired function to the additional channels, which hoses are connected, at their other end, to a connector for connection to a supply unit.

10. A plasma surgical device according to claim 1, in which the housing forms a supply portion, in which said gas supply channel is formed, and a plasma-generating portion, in which said plasma-generating system is provided.

11. A plasma surgical device according to claim 1, in which said cathode is connected to a conductor for connection to a voltage source.

12. A plasma surgical device according to claim 11, in which said conductor is adapted to extend through one of the channels in said housing.

13. A plasma surgical device according to claim 12, in which the conductor extends through a gas supply channel arranged at the centre of said housing.

14. A plasma surgical device according to claim 1, in which said plasma-generating system comprises at least two electrodes, which are insulated from each other by an insulator.

15. A plasma surgical device according to claim 1, in which said at least one electrode is mounted in a holding means made of an electrically insulating material.

16. A plasma surgical device according to claim 15, in which said electrodes are press fitted to said holding means.

17. A plasma surgical device according to claim 15, in which said cathode is arranged in the holding means concentrically with and spaced from an electrode closest to the cathode.

18. A plasma surgical device according to claim 17, in which said cathode is mounted in the holding means by means of a cathode holder, which is press fitted to the holding means.

19. A plasma surgical device according to claim 17, in which an insulating tube of a ceramic material is mounted on the inside of the holding means so as to enclose the cathode.

20. A plasma surgical device according to claim 17, in which the holding means has a connection end, which is connected to said gas supply channel, so that gas is passed through the holding means to the cathode and then through said at least one electrode towards the anode.

21. A plasma surgical device according to claim 20, in which the holding means has an outer shape such as to allow a fluid to flow respectively from and to the additional channels in a space formed between the holding means with said electrode, and the inner wall of the housing at the holding means.

22. A plasma surgical device according to claim 1, in which a gasket is arranged between the anode and the electrode closest to the anode, and the plasma-generating system is arranged in such manner in the housing that the anode is connected to the housing, a predetermined compressive force being applied to the gasket, so that a watertight seal is established between the housing and the anode and electrical contact therebetween is ensured.

23. A plasma surgical device according to claim 1, in which said housing is surrounded by a first contact ring in electrical contact therewith, which contact ring is connected to earth.

24. A plasma surgical device according to claim 23, in which said housing is surrounded by a second contact ring, which is capable of being used to constantly control the earthing of the housing.

25. A plasma surgical device according to claim 24, which comprises a circuit adapted to distinguish the device type by means of the resistance of an indication component.

26. A plasma surgical device according to claim 1, which comprises a handle portion that at least partially encloses said housing to allow easy handling of the device.

27. A plasma surgical device according to claim 1, which has a first button for switching the plasma generator on and off.

28. A plasma surgical device according to claim 27, which, for increased reliability, has a second button.

* * * * *